(12) United States Patent
Wang et al.

(10) Patent No.: US 8,507,451 B1
(45) Date of Patent: Aug. 13, 2013

(54) METHOD FOR THE TREATMENT OF TYPE II DIABETES

(76) Inventors: Zhili Wang, London (GB); Renming Wang, London (GB)

( * ) Notice: Subject to any disclaimer, the term of this patent is extended or adjusted under 35 U.S.C. 154(b) by 53 days.

(21) Appl. No.: 13/279,468

(22) Filed: Oct. 24, 2011

Related U.S. Application Data

(60) Provisional application No. 61/449,890, filed on Mar. 7, 2011.

(51) Int. Cl.
*A01N 43/04* (2006.01)
*A61K 31/70* (2006.01)
*A61K 31/497* (2006.01)

(52) U.S. Cl.
USPC ......................................... 514/25; 514/252.1

(58) Field of Classification Search
None
See application file for complete search history.

(56) References Cited

U.S. PATENT DOCUMENTS

| | | | |
|---|---|---|---|
| 2001/0036917 A1 | 11/2001 | Williams et al. | |
| 2009/0111812 A1 | 4/2009 | Singh et al. | |

FOREIGN PATENT DOCUMENTS

| | | | |
|---|---|---|---|
| CN | 1363274 A | 8/2002 | |
| CN | 1660100 A | 8/2005 | |
| CN | 1660101 A | 8/2005 | |
| CN | 1748675 A | 3/2006 | |
| CN | 101199605 A | 6/2008 | |
| CN | 101816655 A | 9/2010 | |

OTHER PUBLICATIONS

Yucai, The Clinical Effect of Treating DPN with Ligustrazine Phosphate Injection, Journal of Huangshi Institute of Technology, 2006, abstract only.*
Jinhua et al. Study of ligustrazine on chronic complication of diabetes, Modern Journal of Integrated Traditional Chinese and Western Medicine, 2010, abstract only.*
Spuler et al. Ganglioside therapy in experimental diabetic neuropathy, Arzneimittelforschung, Jul. 1988, 38(7): 881-4, abstract only.*
Wang, Jinhua., Hui, Shoudong, "Effect of ligustrazine on treating chronic complication of diabetes", Xiandai Zhongxiyi Jiehe Zazhi, 2010, vol. 19 (14) pp. 1706-1708, China.
Yamamoto, N., Taniura, H., Suzuki, K., "Insulin inhibits a beta fibrillogenesis through a decrease of the GM1 ganglioside-rich microdomain in neuronal membranes", Journal of Neurochemistry, 2010, pp. 628-636, vol. 113 (3), United Kingdom.
Huang, Y., Chen, S., Chen, R., "The protective effect of TMP combined AG on retinal tissue of diabetic rats" Chinese Ophthalmic Research, Apr. 1, 2003 , 21/2, pp. 133-135, China.
Abregu, Adela V., Genta, Susana B., Sanchez-Riera, Alicia N., Sanchez, Sara S., "Immunohistochemical detection of hepatic GM1 and GM2 gangliosides in Streptozotocin-induced diabetic rats", Hepatology Research, Nov. 2002, pp. 256-264, vol. 24 (3), U.S.
Lee, Liang-Ming., Liu, Chi-Feng., Yang, Pao-Pao, "Effect of tetramethylpyrazine on lipid peroxidation in streptozotocin-induced diabetic mice", American Journal of Chinese Medicine, 2002, pp. 601-608, vol. 30 (4), U.S.
Chen, Shaoqiang., Huang, Yan., Chen, Ruihua., Zhang, Geng, "Effects of treatment with ligustrazine and aminoguanidine on VEGF in retina of diabetic rats", Zhongguo Zuzhi Huaxue Yu Xibao Huaxue Zazhi, 2002, pp. 294-296,358, vol. 11 (3), China.
Maruyama, T., Watanabe, K., Yanagawa, T., Kasatani, T., Kasuga, A., Shimada, A., Take!, I., Suzuki, Y., Kataoka, K., Saruta, T., "The suppressive effect of anti-asialo GM1 antibody on low-dose streptozotocin-induced diabetes in CD-1 mice", Diabetes Research, Apr. 1991, pp. 171-175, vol. 16 (4), Edinburgh, Scotland.
Spüler, M., Dimpfel, W., Tullner, H.U., "Ganglioside therapy in experimental diabetic neuropathy", Arzneimittelforschung, Jul. 1988, pp. 881-884, vol. 38 (7), Pro Science Private Research Institute, Linden, Fed. Rep. of Germany.

* cited by examiner

*Primary Examiner* — Layla Bland
(74) *Attorney, Agent, or Firm* — Keith D. Nowak; Carter Ledyard & Milburn LLP

(57) ABSTRACT

A method of treating Type II diabetes utilizing two off-the-shelf drugs.
Intravenous injection of one or both drugs, individually and in combination, can prevent and treat diabetes, restore damaged islet cell functions and reduce or stop the use of oral hypoglycemic agents and insulin.

6 Claims, No Drawings

METHOD FOR THE TREATMENT OF TYPE II DIABETES

PRIORITY AND RELATED APPLICATIONS

This application claims priority to U.S. Provisional Patent Application Ser. No. 61/449,890 filed Mar. 7, 2011, entitled "THERAPY FOR PANCREATIC ISLET B CELL RECOVERY," which is hereby incorporated by reference in its entirety.

BACKGROUND OF THE INVENTION

The number of adults with diabetes has doubled worldwide over the last three decades to nearly 350 million including a threefold increase in the United States. This number includes about 138 million adults with diabetes in China and India, and another 36 million in the U.S. and Russia.

Diabetes is a long-lasting and disabling condition and can lead to kidney failure, blindness, amputation of limbs, and even death if not treated promptly and correctly. Many public health experts consider the rise in diabetes to be more worrying than the rise in high blood pressure rates and cholesterol levels as there are effective drugs for those two conditions, but there are currently no equally effective drugs for the treatment of diabetes.

It is therefore an object of the present invention to provide a novel and very effective drug regimen for the treatment of Type II diabetes not previously available.

It is a further object of the present invention to treat Type II diabetes with a combination of readily available off-the-shelf drugs so that the treatment is cost effective and easily provided to a large number of patients.

Certain prior art publications have used off-the-shelf drugs in an attempt to provide an effective treatment for diabetes. For example, United States Patent Application Publication No. 2001/0036917 proposes a treatment for diabetes through use of monosialotetrahexosylganglioside, also known as GM-1 The present invention also uses GM-1 but the clinical approach used with the present invention is entirely different than what is described in the '917 patent publication. Similarly an article by Lee Liang-Ming in the American Journal of Chinese Medicine, 30(4), pp. 601-608, ISSN:0192-415X, mentions the use of Ligustrazine Phosphate ("LP") for the treatment of diabetes, a second drug used in accordance with the present invention. Again however, this article utilizes an entirely different clinical approach than used with the present invention. Also neither of these two references show or suggest combining GM-1 and LP in the particular manner and with the particular treatment regimen utilized for the treatment of Type II diabetes in accordance with the present invention

SUMMARY OF THE INVENTION

This innovative treatment of diabetics involves two off the-shelf drugs, Monosialotetrahaxosylganglioside <$GM_1$> and Ligustarazine Phosphate (LP). Both are prescription drugs available in the market.

The treatment uses the two drugs individually and in combination. Intravenous injection of one or both drugs, either combined with insulin or not, advantageously achieves the following clinical effects:

1. can prevent and treat diabetes, and to restore Type II diabetes patients' damaged islet cell functions. Patients can reduce or even completely stop the use of oral hypoglycemic agents and insulin;
2. can repair the pancreatic islet cells that are damaged but not yet necrosis;
3. can improve microcirculation and diabetes circulation, prevent and treat diabetic nephropathy, and diabetic retinopathy;
4. can treat the diabetic foot and lower extremity arterial occlusion which is often combined with diabetes, may improve blood circulation and prevent diabetic foot amputation surgery.

DETAILED DESCRIPTION

The present invention uses a combination of LP and GM-1 with the following recommended dosage and treatment regimen:

GM-1; 20-40 mg/day
LP; 40-120 mg/day
Day 1, GM-1 only, Day 2, LP only
Alternate each drug each subsequent day for a total of 14-20 days
Daily use by the patient of a 0.09% sodium salt and water solution.

The foregoing method of treatment has been found to provide superior results over conventional methods for the vast majority of patients having Type II diabetes. However patients with the following profile have been shown to have the best outcome when treated with the inventive method described herein. That patient profile includes:

Less than 10% over normal body weight
Type II diabetes
Pancreatic islet cells that are damaged but not yet in a state of necrosis
No serious heart complications that would prohibit moderate exercise or a special diet
Less than 15 years of diabetic history
Under the age of 65.

This invention has the following two characteristics: First, the use of a unique approach using a combination of two off-the-shelf drugs to treat Type II diabetes patients. Second, this approach is fundamentally different from other methods in terms of medical mechanisms in diabetes treatment. The other approaches found in the prior art are fundamentally different.

The inventive approach, does not use a secretion promoting agent Secretagogues (by promoting B-cell secretion of insulin to lower blood sugar), Biguanides (by reducing the intestinal absorption of glucose in food to reduce blood sugar), α-glucosidase inhibitor (resistance to glucose conversion), or sensitizer (by increasing the sensitivity of insulin receptor).

The inventive approach improves the pancreatic island of microcirculation and improves the deficiency of beta cells. At the same time, the approach also improves and enhances the pancreatic island in the neural endocrine channel and neural peptide activity. It provides the condition and environment for improving the necrosis of pancreatic islet cells which have suffered from injury but not yet completed destroyed. This approach allows the islet cells to be gradually repaired. As a result, the cells can self-generate high quality secretion of endogenous insulin.

Therefore, through the joint application in the clinical treatment of the two drugs described above, not only can the invention effectively control blood sugar in patients with Type II diabetes, but also in maintain stable blood sugar within the normal range of cases, decreased oral hypoglycemic agents and insulin dose, up to complete cessation of medication, while at the same time maintain blood sugar within the normal range.

Intravenous injection of various combinations of the above mentioned drugs is the method of the present invention for the clinical treatment of diabetes patients. A patient profile (described above) is most advantageous for the most effective treatment of this inventive method. If patients meet the indications described by the profile, there is a probability of 95% or more for the restoration of islet cells to certain degrees. The results of the treatment include the following improvements after the treatment:

Patients greatly reduce the use of drugs or insulin or oral hypoglycemic drug dosage.

Patients' blood sugar is likely to remain at a satisfactory state.

Islet cells have been significantly repaired, that is, to achieve complete cessation of clinical insulin injections.

The probability of completely stopping the use of oral hypoglycemic agents can be achieved in more than 80% of patients treated.

Case Report 1

Beijing Chaoyang Diabetes Hospital ("BCDH")

The patient was admitted to hospital twice. The first time after treatment, he stopped the use of insulin or oral medicine for 3 months.

Huang xx: Male, 34 yrs. old (30 yrs. old when diagnosed), Office Clerk, married. (Case No. 6623)

Complaints: weight loss 2 yrs, fingers anaesthesia for 1 year, fatigue for 1 month.

History of present disease: The patient was in hospital for acute hepatitis, with weight loss (10 kg in 1 year), his fasting glucose was 7.3 mmol/L, PBG was 11.5 mmol/L, he was diagnosed with diabetes and started diet control and doing exercise. He went to Xiehe hospital for a medical examination and his fasting glucose was 11 mmol/L. 10 days later his fasting glucose was 16 mmol/L, so he was admitted to BCDH for further treatment.

Medical history: Hepatitis B for 4 yrs., cured. Hypertention for 2 yrs., the highest BP was 132/100 mmHg, untreated. No heart disease.

Personal history: Smoking for 17 yrs., 20 cigarettes per day. Drinking for 11 yrs., 150 g alcohol per day for 2 yrs.

Family history: Father and mother are diabetics.

Physical Examination

T 36.1° C., P 76 times/min, R 18 times/ml, BP 140/90 mmHg

H 176 cm, W 79 kg, BMI 25.5 kg/m$^2$

No abnormalities in heart, lungs, abdominal and limbs.

Lab Results

Blood routine: normal.

Urine routine: normal.

Biochemistry: UA: 453 umol/L, CHO: 7.9 mmol/L, TG: 5.12 mmol/L, HDL-C: 2.05 mmol/L, LDL-C: 3.87 mmol/L, GSP: 423 umol/L.

HbA1c: 11.9%.

Initial Insulin Release Test Results:

| OGTT | 0' | 30' | 60' | 120' | 180' |
| --- | --- | --- | --- | --- | --- |
| Glu (mmol/l): | 11.97 | 16.01 | 21.71 | 24.09 | 23.41 (AUC 63.1) |
| Ins (Uu/ml): | <5 | <5 | 7.49 | 15.43 | 10.30 |
| c-p (ng/ml): | 0.57 | 0.73 | 1.00 | 1.74 | 1.59 (AUC 3.79) |

Treatment

Glucose level was controlled with insulin and infusion treatment to improve the microcirculation and the nerve system. Four weeks later insulin was stopped and his glucose was controlled. The patient was then discharged. Subsequently the patient controlled his glucose only by diet and exercise, and glucose is ok. He was admitted to BCDH again for further control and the repairment of B-cell function. Here is the latest insulin release test results:

HbA1c: 6.7%.

Initial Insulin Release Test Results:

| OGTT | 0' | 30' | 60' | 120' | 180' |
| --- | --- | --- | --- | --- | --- |
| Glu (mmol/l): | 7.18 | 9.89 | 13.32 | 14.05 | 14.42 (AUC 37.99) |
| Ins (uU/ml): | 7.64 | 18.50 | 44.72 | 56.42 | 53.27 |
| c-p (ng/ml): | 1.61 | 2.13 | 4.34 | 5.22 | 5.08 (AUC 12.48) |

Biochemistry: GGT: 57U/L, UA: 506 umol/L, CHO: 4.7 mmol/L, TG: 1.49 mmol/L, HDL-C: 1.49 mmol/L, LDL-C: 2.53 mmol/L, CRP-hs: 9.6 mg/L.

In summary, with the treatment described herein and diet control, his B-cell function was improved.

Case Report 2

Beijing Chaoyang Diabetes Hospital

The patient was admitted to hospital 4 times. The first time the insulin dose was reduced gradually from 24 u/day to 5 u/day, then he took insulin injection (5 u) for 1 month. Glucose was controlled by diet and exercise after meals. After the fourth time, bodyweight, glucose and diabetes complications such as kidney, liver, nervous system were much improved.

Wang xx: Male, 52 years old (44 yrs. old when first diagnosed), Officer, married. (Case No. 6459)

Complaints: hyperglucose for eight years.

History of present disease:

The patient was diagnosed with diabetes after a medical examination (without symptoms), his fasting glucose was 8 mmol/L, post meal was 12 mmol/L. He took oral medicine (Metformin & Acarbose) before he came to BCDH.

Past medical history: hypertension for 20 yrs., the highest BP was 160/100 mmHg, took medicine and BP was controlled. Myocardial ischemia for 20 yrs., found by ECG, without chest tightness or chest pain, sometimes took some Chinese traditional medicine.

Personal history: smoking for 35 yrs., 10 cigarettes per day. Seldom drank alcohol.

Family history: Father, mother, daughter are diabetics.

Physical Examination

T 36.5° C., P 62 times/min, R18 times/min, BP 130/80 mmHg

H 178.5 cm, W 91 kg, BMI 25.40 kg/m$^2$

No abnormalities in heart, lungs, abdominal and limbs.

Lab Results

ALT: 61U/L, TG: 3.68 mmol/L.

Uric MA: 57.0 mg/L (Normal range: 0-30 mg/L).

Nerve system: diabetes neuropathic.

HbA1c: 6.2%.

| OGTT | 0' | 30' | 60' | 120' | 180' |
|---|---|---|---|---|---|
| Glu (mmol/l): | 7.23 | 8.07 | 13.09 | 12.15 | 10.58 |
| Ins (uU/ml): | 7.37 | 9.49 | 36.84 | 29.85 | 31.28 |
| c-p (ng/ml): | 0.98 | 1.42 | 3.33 | 3.25 | 4.06 |

Treatment

Insulin pump treatment was started for him. In 17 days the insulin dose was reduced gradually from 24 u/day to 4.6 u/day, his weight reduced gradually by 4.5 kg, then he changed to insulin injection instead. When discharged his glucose was well controlled with 5 u insulin and diet control and exercise after meals. The last time he was admitted to BCDH for further control and the repair of B-cell function his test results were:

HbA1c: 6.0%.

| OGTT | 0' | 30' | 60' | | 180' |
|---|---|---|---|---|---|
| Glu (mmol/l): | 5.48 | 10.97 | 12.75 | 8.30 | 6.21 |
| Ins (uU/ml): | 12.49 | 47.00 | 57.61 | 32.48 | 16.80 |
| c-p (ng/ml): | 0.97 | 2.51 | 3.42 | 3.61 | 2.87 |

In summary, after treatment in accordance with this invention and diet control, his B-cell function was improved.

Case Report 3

Beijing Chaoyang Diabetes Hospital

The patient was admitted to BCDH twice. The first time the insulin dose was reduced gradually from 24 u/day to 2.7 u/day, and the glucose was controlled by diet and exercise after meals. When checked the second time, body weight, glucose and diabetes complications such as heart, liver, were much improved.

Sun XX, Male, 54 years old (47 yrs. old when diagnosed), Teaching Staff, Married. No family history of diabetes. (Case No. 8473)

Complaints: thirsty, polyuria for 7 yrs.

History of present disease:

The patient drank more than 5000 ml of water a day, polyuria. He was diagnosed with diabetes at the local hospital and used insulin "Humalog 25", 45 u/day for 4 yrs. before coming to BCDH.

Past medical history: no hypertension or heart disease.

Personal history: 20 cigarettes/day, but stopped for the last 4 yrs. Seldom drinks alcohol.

Family history: no diabetes.

Physical Examination

T 36.5° C. P 64 times/min R18 times/min BP 130/80 mmHg

H 171 cm, W 85 kg, BMI 29.07 kg/m$^2$

No abnormalities in heart, lungs, abdominal and limbs.

Treatment

Initial Insulin Release Test Results:

| OGTT | 0' | 30' | 60' | 120' | 180' |
|---|---|---|---|---|---|
| Glu (mmol/l): | 8.25 | 12.70 | 15.53 | 17.72 | 11.49 |
| Ins (uU/ml): | 53.65 | 85.13 | 75.51 | 67.53 | 82.81 |
| c-p (ng/ml): | 2.81 | 3.56 | 3.99 | 3.77 | 4.78 |

HbA1c: 7.0%

Treatment

Glucose was controlled with an insulin pump and he was treated with infusion to improve the microcirculation and the nerve system. In 22 days his insulin use reduced gradually from 24 u/day to 2.7 u/day, had a gradual weight loss of 6.5 kg, glucose was well controlled by diet and exercise after meals. Patient was admitted to BCDH once again for further control and the repairment of B-cell function. During the last 5 months, he lost 11 kg after discharge. The latest insulin test results are: HbA1c: 6.1%.

| OGTT | 0' | 30' | 60' | 120' | 180' |
|---|---|---|---|---|---|
| Glu (mmol/l): | 4.95 | 8.25 | 9.04 | 8.30 | 4.87 |
| Ins (uU/ml): | 19.04 | 47.98 | 35.15 | 61.82 | 18.01 |
| c-p (ng/ml): | 1.88 | 5.40 | 4.85 | 7.11 | 3.85 |

H 171 cm, W 67.5 kg, BMI 23.30 kg/m$^2$

In summary, after our treatment in accordance with the invention and diet control, his B-cell function was improved.

Case Report 4

Beijing Chaoyang Diabetes Hospital

The patient was admitted to BCDH for the repair of his B-cell function and severe damage of the liver. After 6 months, his health index became much better than before.

Salih, Male, 59 yrs. old (45 yrs. old when diagnosed), Ambassador, married. (Case No. 7008)

Complaints: hyperglucose 14 years, fatigue for 2 months.

History of present disease:

The patient was diagnosed with diabetes according to medical examination (without symptoms), he had taken three kinds of oral medicine (Metformin & Acarbose & Glipizide) before coming to BCDH, but his glucose was not under control (FBG 10-15 mmol/L). Two months ago (after taking Atorvastatin for 1 month), he felt fatigue and went to see a doctor. His blood test showed that his liver function was not good, so he stopped taking Atorvastatin. However, the symptoms didn't get better. He lost 7 kg of body weight in 14 years.

Past medical history: hypertension for more than one year, taking medicine, but seldom measured his BP.

Personal history: no cigarettes or alcohol.

Family history: mother and sisters have diabetes.

Physical Examination

T 36.4° C., P 80 times/min, R 17 times/min, BP 140/90 mmHg

H 173 cm, W64 kg, BMI 21.38 kg/m$^2$

No abnormalities in heart, lungs, abdominal and limbs.

Lab Results

ALT: 366U/L, AST 138U/L, ALP 138U/L, GGT 350U/L; UricB2-MG: 0.75 mg/L (Normal range: 0-0.3 mg/L).

HbA1c: 10.9%.

Nerve system: diabetes neuropathic damage.

Initial Insulin Release Test Results:

| OGTT | 0' | 30' | 60' | 120' | 180' |
|---|---|---|---|---|---|
| Glu (mmol/l): | 7.61 | 7.63 | 13.60 | 18.77 | 17.06 |
| c-p (ng/ml): | 0.76 | 0.45 | 0.59 | 1.24 | 1.43 |

Treatment

We started insulin pump treatment for him, and provided treatment for the liver problem. He was also treated with infusion to improve the microcirculation and the nerve system. One month later he stopped the insulin pump and changed to insulin injection. Insulin release test results after six months are:

| OGTT | 0' | 30' | 60' | 120' | 180' |
|---|---|---|---|---|---|
| Glu (mmol/l): | 6.67 | 7.96 | 14.76 | 22.33 | 22.19 |
| c-p (ng/ml): | 0.60 | 0.74 | 1.35 | 3.04 | 3.21 |

W 68 kg
ALT: 38U/L, AST29U/L, ALP5OU/L, GGT 62U/L;
Uric 32-MG: 0.34 mg/L (Normal range: 0-0.3 mg/L).
HbA1c: 7.0%

In summary, after treatment in accordance with the invention and diet control, his B-cell and liver function were improved.

Case Report 5
Beijing Chaoyang Diabetes Hospital

The patient came BCDH when he was diagnosed with IGT, and OGTT showed that FBG 7.64 mmol/L, 2H BG 14.18 mmol/L. He was diagnosed with T2DM, and admitted to BCDH six times. After treatment in accordance with the invention, he stopped using insulin or oral medicine, and his glucose and diabetic retinal complication were controlled.

WU XX, Male, 47 yrs. old (43 yrs. old when diagnosed), CEO, Married. No family history of diabetes. (Case No. 5593)

Complaints: weight gain for 9 yrs., hyperglucose for 4 yrs., blurred vision 15 days.

Past medical history: hypertention for 1 year, no heart disease.

Personal history: 10 cigarettes per day. Consumed alcohol for 10 years with 150-200 g per day.

Family history: no diabetes.

Physical Examination

T 36.4° C., P 83 times/min, R 17 times/min BP 165/115 mmHg

H 176 cm, W97 kg, BMI 31.3 kg/m²

No abnormalities in heart, lungs, abdominal and limbs.

Lab Results

HbA1c: 10.6%.

Fundus: diabetic retinal disease (Stage I).

Treatment

He was treated with an insulin pump and with infusion to improve the microcirculation and the nerve system, which controlled diabetic retinal disease. Two weeks later, his insulin reduced gradually from 9 u/day to zero. He lost 2 kg of weight. After the treatment, his glucose was well controlled only by diet and exercise after meals. Bleeding spots were absorbed.

In summary, after treatment in accordance with the invention, his B-cell function and diabetic complications were improved during his follow-up visits.

Case Report 6
Beijing Chaoyang Diabetes Hospital

Li xx: Female, 38 years old. Ethnic: Han.

Complaints: High blood sugar for two years, excess of water intake and urine, weight loss for one year.

History of present disease: diagnosed high blood sugar two years ago. fasting glucose was 14 mmol/l. Within last year, had dry mouth, excess of water and urine, weight loss of 10 kg. Took insulin injection of 6 u before being admitted BCDH. Fasting glucose was 14.6 mmol/l.

Headache from time to time, occasionally flustered, chest tightness, abdominal distension, constipation.

Medical history: highest BP for five years 150/110 mmHg, Oral acid Levamlodipine Personal history: Smoking for over 10 yrs., 10 cigarettes per day.

Menstrual obstetrical history: from 14 years old with normal menstrual regularity, no children.

Family history: Mother is diabetic.

Physical Examination

T 36° C. P, 70 times/min, R 17 times/min, BP 130/80 mmHg

H 167 cm, W 84.5 kg, BMI 30.3 kg/m²

Lab Results

HbA1c: 10.3%

Fundus: diabetic retinal disease (Stage I)

| | 0' | 30' | 60' | 120' | 180' |
|---|---|---|---|---|---|
| OGTT (mmol/l): | 13.7 | 15.78 | 21.82 | 24.92 | 23.15 |
| Ins (Uu/ml): | 15.20 | 18.25 | 29.23 | 28.31 | 27.58 |
| c-p (ng/ml): | 2.01 | 2.49 | 2.79 | 3.87 | 3.93 |

Treatment

We treated her in hospital for 19 days, with insulin max 35.9 u, and 11.8 u before discharge. Weight loss of 2.5 kg.

Lab Results Before Discharge:

Urine: normal.

Biochemistry All items: CHO: 3.5 mmol/l, TG: 1.10 mmol/l, LDL-C: 2.26 mmol/l.

Follow-up: weight loss of 3 kg in 3 months after treatment. No longer taking insulin and any oral hypoglycemic agents, blood glucose control was good.

The foregoing case histories clearly demonstrate the efficacy of the present invention for the treatment of Type II diabetes. No other known treatment provides equal results for patients based on the use of two off-the-shelf drugs. The present invention therefore provides a cost effective and widely available treatment for Type II diabetes not available with prior art treatments.

The description of certain embodiments of this invention is intended to be illustrative and not limiting. Numerous other embodiments will be apparent to those skilled in the art all of which are included within the broad scope of this invention as particularly set forth in the appended claims.

The invention claimed is:

1. A method of treating Type II diabetes in a subject by administering GM-1 at the rate of 20-40 mg/day and Ligustrazine Phosphate at the rate of 40-120 mg/day to the subject in need of such treatment, wherein said GM-1 and said Ligustrazine Phosphate are administered intravenously.

2. A method in accordance with claim 1 wherein said GM-1 is administered during the first day of treatment.

3. A method in accordance with claim 2 wherein only said Ligustrazine Phosphate is administered during the second day of treatment.

4. A method in accordance with claim 3 wherein said GM-1 and said Ligustrazine Phosphate are administered on alternate days.

5. A method in accordance with claim 4 wherein said GM-1 and said Ligustrazine Phosphate are administered for a total of 14-20 days.

6. A method in accordance with claim 5 wherein the administration of said GM-1 and said Ligustrazine Phosphate is combined with daily use by the patient of a 0.09% sodium salt and water solution.

* * * * *